United States Patent [19]

Aemmer

[11] 4,430,720

[45] Feb. 7, 1984

[54] CLEANING YARNS AND ASSESSING YARN DEFECTS

[75] Inventor: Peter F. Aemmer, Wettswil, Switzerland

[73] Assignee: Zellweger Uster AG, Uster, Switzerland

[21] Appl. No.: 212,708

[22] PCT Filed: Dec. 12, 1979

[86] PCT No.: PCT/CH79/00159

§ 371 Date: Nov. 10, 1980

§ 102(e) Date: Nov. 10, 1980

[87] PCT Pub. No.: WO80/01955

PCT Pub. Date: Sep. 18, 1980

[30] Foreign Application Priority Data

Mar. 16, 1979 [CH] Switzerland .................. 2491/79

[51] Int. Cl.³ .................................................. G06F 15/46
[52] U.S. Cl. .................................. 364/552; 364/470; 73/160
[58] Field of Search ............... 364/470, 552, 554, 563, 364/550; 57/81, 264, 265, 362; 235/92 PD, 92 DN; 73/159, 160; 28/185, 187

[56] References Cited

U.S. PATENT DOCUMENTS

| | | | |
|---|---|---|---|
| 3,594,558 | 7/1971 | Loepfe | 364/470 |
| 3,731,069 | 5/1973 | Goto et al. | 364/470 |
| 3,892,951 | 7/1975 | Stutz | 364/563 |
| 4,007,457 | 2/1977 | Aeppli | 73/160 |
| 4,030,082 | 6/1977 | Goto | 364/470 |
| 4,045,659 | 8/1977 | Akagawa et al. | 73/160 |
| 4,051,722 | 10/1977 | Feller | 364/552 |
| 4,140,898 | 2/1979 | Gasser et al. | 235/92 PD |
| 4,173,787 | 11/1979 | Katona et al. | 364/550 |
| 4,195,345 | 3/1980 | Artzt et al. | 364/470 |
| 4,246,748 | 1/1981 | Artzt et al. | 364/470 |

*Primary Examiner*—Gary Chin
*Attorney, Agent, or Firm*—Antonelli, Terry & Wands

[57] ABSTRACT

A method of cleaning yarns and evaluating yarn defects by means of digital technology is based on the fact that the physiological perception arising from observation of yarn defects, both as to cross section as well as in length, is approximately proportional to the logarithm of the physical expansion of such yarn defects, and also of the fact that yarn defects are statistically rare events. Signals corresponding to the yarn cross section or diameter are converted to and processed in the logarithmic scale. For purpose of analysis of these converted signals, a tolerance range and a system of tolerance zones arranged in both the transverse dimension and the longitudinal dimension is defined about the yarn. Different analysis criteria are applicable for those zones, and only those signals are analyzed which have directly exceeded or fallen short of at least one of the zone limits, with the result that the need for signal processing capacity is reduced. By subdividing the method into a rigidly-clocked data scanning process and into at least one additional signal processing process decoupled from the data scanning process temporarily by a data buffer action, the requirement peaks are processed by one or more processors whose average processing capacity is considerably smaller than the peak requirement.

12 Claims, 5 Drawing Figures

CLEANING YARNS AND ASSESSING YARN DEFECTS

This invention relates to cleaning yarns and to assessing yarn defects.

Apart from specific cases in which special yarn is desired to produce particular fashion effects, it is considered that the smoother the yarn is with respect to fluctuations in its cross section or diameter, the better will be the quality and the price which can be obtained for such yarn on the market. The appearance of such yarn quality is typically measured with the aid of yarn charts or electronic devices operating on the basis of known evaluation methods developed over the years especially for this purpose. Yarn cleaning apparatus are purposely used in a known manner for improving the quality of yarn on the basis of such measurable qualitative features. Apparatus of this type operates to cut out those yarn defects from the yarn during a rewinding process which exceed certain limiting values of one or more qualitative features.

It has become generally standard practice to consider the sporadically appearing visible irregularities in yarn as separate features along the total length of the yarn as compared to the statistical variations of the yarn cross section or diameter which appear far more regularly and consistently. Here, the distinction is made between thickenings of approximately one millimeter to a few centimeters (neps, slubs), between longer slubs of a few centimeters to approximately 50 cm plus (double threads, slubs) and thin places of a few centimeters to several meters in length.

The subjective perception or appearance, which is caused by the sporadic yarn defects described above, in the dimension of cross section or diameter of the yarn as well as in the dimension of length, is such that deviations in respect of a predetermined diameter on the one hand and with respect to a length of approximately 2 to 50 cm on the other hand very closely relate logarithmically to the quantity of these deviations. In other words, the subjective disturbing effect of a defect as perceived by the human eye increases or decreases approximately in proportion, to the logarithm of the physical expansion of the defect in one of the two dimensions thereof. In an evaluation of such defects, this would mean that, for example, every doubling of a defect feature in one dimension or the other corresponds to an increase of the disturbance sensitivity by only one factor. This identification can be observed effectively with the aid of defect quantization scales which have been used already in practice. In this regard, it is also known in that physiological perceptions, as for example perceptions of sound volume and light intensity are also related to the corresponding physical influence factor approximately in a logarithmic relationship.

Thus, the approximate logarithmic relationship between subjective a physiological perception and the objective state of sporadically arising yarn defects is known. This is acknowledged among other places in the customary practice of evaluating and classifying yarn defects into defect classes. However, up until now, no methods have been known in the area of yarn analysis and cleaning which intentionally make use of this logarithmic relationship and the relatively rare appearance of yarn defects for effecting simplification of these devices or for increasing the productive capacity of such devices. Of course, as long as techniques are carried out with use of circuitry based on analog technology for yarn analysis, there is no need to refer to these known relationships since the customary signal analysis using linear low pass filter elements and non-linear threshold value discriminators could hardly be improved in terms of simplicity.

It is a different matter with digital signal processing, however, involving the use of micro processors, processor elements and addressable memories. In this regard, the known digital methods for yarn analysis and cleaning are based on a signal processing which in the simplest way may be defined as a simple reproduction of the analog technology using digital means. However, these methods do not necessarily lead to a very advantageous solution since the digital technology has been basically subjected to different restrictions than the customary analog technology up until now from the point of view of complexity and cost of equipment.

The subject of the method hereinafter described has a feature in that the approximate logarithmic relationship, known per se, between the subjective defect perception as apparent to the human eye and the corresponding state of such yarn defects, which appear sporadically as lengthwise slubs or thin places, is used for increasing the efficiency or for decreasing the complexity and cost of electronic devices for measuring and evaluating, as well as for cleaning out, yarn defects which exceed certain limiting values in one or more dimensions. Although the invention can also be applied to analog systems, the method according to the invention is particularly advantageous for devices which operate on the basis of digital technology regardless of whether they are hard wired or programmed logic devices.

The present invention takes these considerations into account and relates to a method of cleaning yarns electronically and of assessing yarn defects by means of digital technology using sensors which emit signals proportional to the yarn cross section or to the diameter of the yarns, and converting these signals to logarithmic values. By this means the necessary signal analyzing devices for this purpose may be restricted to equipment having a minimum technical quality necessary to perform the required detection of yarn defects at minimum cost. In other words, the present invention makes possible the use of lower cost equipment, as will be explained in more detail hereinafter.

As is known, a direct current is produced at the measuring head for the yarn, which can be designed for example as a precision capacitor with an HF-oscillator and a demodulating circuit, which direct current is substantially proportional to the cross section of the yarn present in the precision capacitor and to a material-dependent multiplying constant.

In known apparatus for yarn cleaning and classification, without considering the rather regularly appearing cross section deviations, but considering the dielectric characteristics of the yarn material represented by the material characteristics, a dynamic ratio is produced from the smallest to the greatest signal of approximately 1:100, for the region of the nominal cross section provided at a customary measuring head alone. For the yarn deviations to be scanned in terms of measuring, in respect to the nominal cross section, the dynamic ratio is approximately 1:40 between the smallest signal at a thin place (approximately 25% of the nominal cross section) and the greatest signal at a slub (approximately 1000% of the nominal cross section). Thus, altogether a maximum signal dynamic ratio of 1:4000 is produced.

If, for example, a resolution of 10% is also required for the smallest signal, then a signal volume of 1:40,000 is produced together with the signal dynamic ratio mentioned above.

If this signal volume is desired to be quantized a linear manner and represented integrally and in binary form, then a word length of at least 16 bits is required.

The complexity, and thereby the expense, of digital signal processing is substantially dependent on the word length required for the representation of the signals. A method of digital signal processing, which functions with a signal coding requiring shorter word lengths with an approximately constant number of operational steps for a given machine, thus has an economical (in terms of expense) advantage in contrast to a method which requires a representation of the same signals by means of a longer word length. In addition, the cost of digital equipment in a digital processing system depends not only on the required processing accuracy, but also on the required processing speed. Thus, where it is possible to operate at slower processing speeds, less expensive digital equipment can be used.

The known methods of yarn analysis and cleaning by means of digitally functioning devices scan the yarn cross section or diameter by using measuring heads of the type which produce an analog signal output. The pre-processing of the analog signal is effected by means of analog elements (e.g. low pass filters, zero balance circuits among others), and the measuring signal is then subjected to an A/D conversion and then processed further using digital circuits.

The method according to the invention differs from this traditional technology in that before one of the first steps of the digital signal processing, the signal representation is converted from the linear scale to the logarithmic scale or to a scale approximate or similar to this. As a result, multiplications or divisions respectively of signal values with constants and parameters can thereby be effected simply and inexpensively on the basis of additions or subtractions, respectively.

In the previous numerical example, a ratio of 1:40 was assumed in the cross section from the smallest signal (at a thin place) to the greatest signal (at a slub), based on a yarn of a constant nominal diameter. With a relative resolution of 0.1, the conversion from the linear into the logarithmic scale must therefore be effected in constant 10%-steps. The number n of the required steps is calculated according to the formula $$n = (\log 40/\log 1.1) \cong 39$$

If it is desired to divide up the total dynamic ratio range of 1:4'000 into 10%, the number of the necessary steps is calculated at:

$$n = (\log 4'000/\log 1.1) \cong 87$$

In the first case, a word length of at least 6 bits is necessary for the digital representation as an integral binary word and in the last case a word length of at least 7 bits is required. In this example, it can be seen that the minimum required word length is thereby reduced by more than a factor of 2 in contrast to the above mentioned value of 16 bits required for the signal processing method according to traditional known technology.

Bearing in mind the foregoing considerations, the present invention provides a method of assessing yarn defects using digital technology which avoids the onerous cost requirements of similar systems in the prior art.

In this regard, one aspect of the present invention is based upon the recognition that there is a logarithmic relationship between the subjective perception of yarn defects and the three-dimensional sizes of those yarn defects. Thus, the present invention proposes that the meaasuring signal which has a magnitude proportional to the cross section or diameter of the yarn under inspection be transformed into a logarithmic or quasi-logarithmic signal prior to signal analysis. This produces several unobvious advantages. First of all, by thus compressing the measuring signal, it is no longer necessary to provide a digital system capable of operating on sixteen bit words since excessive peaks in the original signal will be reduced leaving threshold values within small limits. In the example provided above, it is seen that the present invention is capable of reducing the required word length to only six or seven bits, permitting the system to operate with eight bit processors, rather than the more expensive sixteen bit processors. In addition, in the signal processing itself, the normalizing of the signals which typically involves multiplication or division operations can be carried out with the converted signals using addition or subtraction operations, thereby clearly facilitating the signal processing. Thus, the method of the present invention differs from the traditional approach of the prior art in that, before digital signal processing is effected, the signal representation is converted from the linear scale to the logarithmic scale or to a scale approximate or similar to this.

From the fact that yarn defects appear relatively seldom and are apparent in the form of longitudinal slubs and thin places, it can be concluded that whenever a yarn which is faultless in the sense of detectable defect perceptions is wound through the sensor, the information rate is practically zero and then, when a defect appears, the information rate rises, but this only happens to a very limited extent. The information rate is also limited by the state of the yarn defects as substantially longitudinal slubs and thin places in the sense that defects can indeed become visible relatively quickly (when unwinding through the sensor), but can then exhibit a relatively long inertia, until they disappear again relatively quickly. The information rate is also limited in that the length of yarn defects, as previously explained, is only perceived subjectively by the human eye approximately in the logarithm of their physical expansion. Therefore, the longer the length expansion of yarn defects has been observed since the time of their respective start through the signal processing process, the rougher will be the analysis that can be effected through this process in the longitudinal direction without an excessive defect appearing in the subjectively relevant result.

A signal processing method which is constantly set for a fast reaction, as must be the case for the appearance of a defect is clearly unnecessary from the point of view of the signal processing requirements, in the stationary or quasi-stationary case, either where no deviation appears which could be perceived as a yarn defect or where such deviations last for a substantial period of time without substantial change.

In analog technology, there is very little tolerance in adapting a signal processing method to a load fluctuating with time through the course of a processing requirement justified by the result of the processing. Signal processing methods for yarn analysis and cleaning operating on the basis of analog technology are then all performed so that events which appear rarely per se could also appear more frequently or all the time.

The state of digital technology now presents the opportunity by means of cheaper addressable data memories and available methods of computer technology of designing signal processing methods for fluctuating loads such that a processor carrying out a method of this type can be dimensioned for a productive capacity which is smaller than would be necessary for the case involving only short-time appearing peak strains. Since in electronic yarn cleaning and yarn defect classification according to this invention a short time requirement exists, processors for signal processing based on this fact can be used and this results in considerable advantages with respect to cost-effectiveness of the apparatus in contrast to traditional technology.

Since the time itself cannot be compressed or expanded, according to the present invention, means are provided in which the data is stored in a buffer store which forms a queue for such data.

Thus, a second feature of the present invention relates to the recognition that defects in the yarn occur relatively seldom, i.e., are statistically distributed, in the yarn with the result that analysis typically need not be completed immediately upon detection of the fault. However, if two or more faults occur within short intervals, rapid analysis of one fault to prevent loss of data relating to the succeeding fault would typically require the provision of hgh speed digital processing circuitry. Accordingly, it is proposed in accordance with the present invention that the analysis of yarn signals comprise plural successive processes which operate independently of one another and between which the data from the previous process is buffered or stored until the succeeding process requires that data. By this means, slower, and therefore less expensive, digital processing equipment can be utilized.

Explained by a simple example derived from the technology of known apparatus for electronically cleaning yarns and classifying yarn defects, a data reservoir (buffer store) is constantly fed with signal data produced by the measuring head by means of a primary process, while a second process then constantly empties the data reservoir (buffer store) by withdrawing the data previously stored therein. The first process fulfills the function of measuring value processing on a real time basis by scanning at the measuring points and of any necessary signal preparation (e.g. synchronisation with a process which does not run at a constant rate, zero correction and drift correction, linearisation of the sensor characteristic, A/D-conversion, signal compression for example according to the method mentioned above of converting the signal representation from the linear scale to the logarithmic scale), and finally stores and arranges the prepared measuring data in the data reservoir (buffer store).

The second process removes the pre-processed measuring data from the above mentioned data reservoir (buffer store) and subjects this to signal analysis. If, as assumed here, it is a matter of analysing rarely appearing defects, the signal analysis will most frequently come to a negative result. This is to be established respectively with few operational steps, therefore the analysis process takes place quickly. In rarer cases, the error analysis will hit upon a positive result which is to be analysed more exactly. As a result of a detailed analysis of this type, other processes are to be optionally performed. For this purpose, several operational steps are generally required, and the analysis process takes place more slowly as a result of this.

An improved load balance can be achieved by means of the buffer-effect explained above, in that the processor, in which the second mentioned process takes place, is dimensioned so that averaged, over a given period of time, it can work off the measuring data material supplied in the data reservoir (buffer store) with sufficient reliability. In rarer cases, where a larger number of defects are to be analysed, a greater backlog (queue) will appear in the data reservoir (buffer store) which backlog is decreased again during the remaining time.

By the distribution of the analyzing time over the entire duration of the test, the various processors involved in the analyzing of the yarn signals can be kept at a moderate size and less cost than if completion of the analysis were required during the occurrence of each detected value. Thus, the present invention provides for a reduction in the cost of the digital processing system not only by a reduction in the required word length of the digital signals being processed, but also by signal selection and buffering to reduce the speed requirements of the digital circuitry.

The statistical balance in defect analysis of processes of this type can be improved in that several measuring heads are cyclically analysed in the second mentioned process, since in practice, statistical independences can be assumed with respect to the defects appearing between the measuring points. Or conversely, it is possible to process the resulting data of a greater number of measuring heads as a result of the method according to the invention, by using a processor of a given capacity.

Even though only two processors decoupled by an intermediate data reservoir (buffer store) were discussed in the above embodiments for the sake of simplicity, those skilled in the art will find it advantageous in certain cases—without deviating from the method of the invention—to implement the first and/or the second of the processes mentioned above by two or more partial processes decoupled from each other by means of data reservoirs (buffer stores).

The invention will now be explained in more detail with reference to the accompanying drawings in which.

Figure 1:
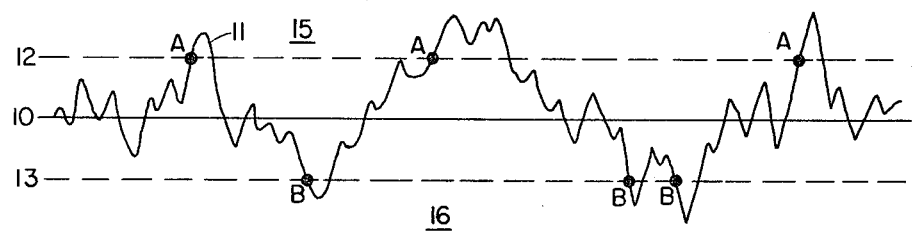
FIG. 1 is a diagram representing a yarn section having tolerance limits in the transverse dimension of the yarn.

FIG. 1 shows a representation, known per se, of the cross section of a yarn as a signal curve 11 varying about a mean 10, as drawn for example by a recorder to the input of which an electrical signal is supplied by a measuring device scanning the cross section of the yarn. FIG. 1 also shows an upper tolerance limit 12 and a lower tolerance limit 13, the exceeding of which is to be evaluated in the signal curve 11. As soon as the signal curve 11 has exceeded these tolerance limits (point A or B), it passes into one of the regions 15,16.

The information that the signal curve 11 is exceeding the given tolerance limits is interpreted in accordance with the digital technology in that the amplitude of the signal curve 11 is scanned at a given clock frequency and every amplitude value is thereby compared with a value representing the tolerance limit.

Figure 2:
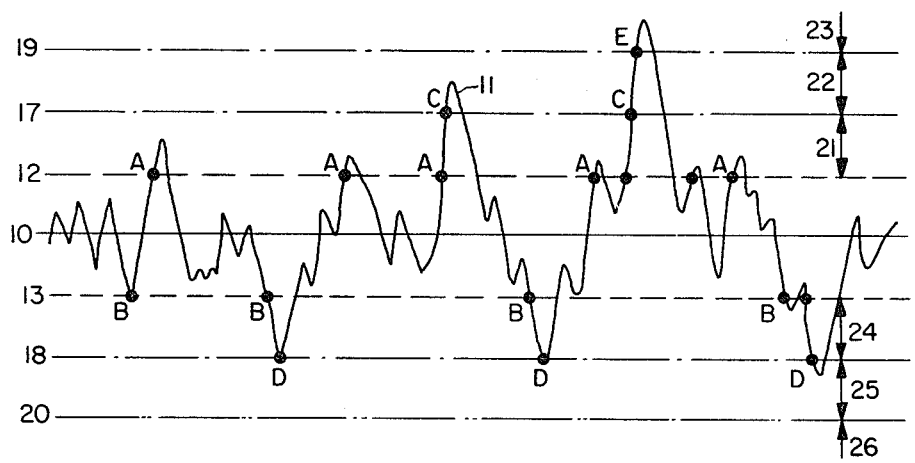
FIG. 2 is a diagram representing a yarn section having an evaluation zone also in the transverse dimension of the yarn.

According to the embodiment of the method shown in FIG. 2, the regions 15 and 16 outside the tolerance limits 12 and 13 through the setting of other tolerance limits 17 and 19 or 18 and 20 are divided into transverse zones 21,22,23,24,25 and 26. Each of these transverse zones now forms a criterion for the fact that a certain effect of the relevant relative deviation is expected by the entrance of the signal curve 11 into the next transverse zone or when the signal curve leaves the previous transverse zone.

Figure 3:
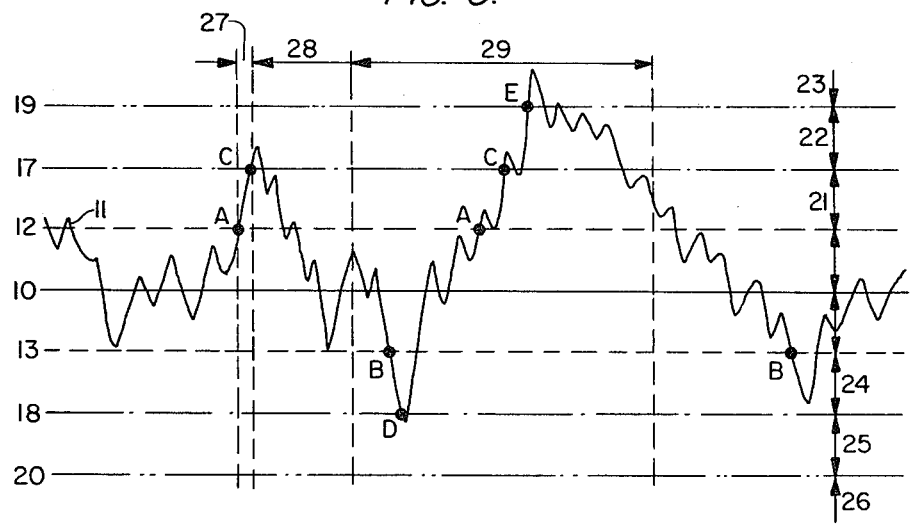
FIG. 3 is a diagram representing a yarn section having evaluation zones in the transverse dimension and in the longitudinal dimension of the yarn.

According to the further development of the method of the invention shown in FIG. 3, the longitudinal dimension of the yarn is now also divided up into longitudinal zones 27,28 and 29. The longitudinal zone 27 is defined for example in that it begins respectively when the signal curve 11 has again first exceeded the upper tolerance limit 12 or the lower tolerance limit 13 after a faultless yarn section (points A,B). The signal is firstly analysed for short defects in this longitudinal zone 27 by using the second process mentioned above, in that for example at each scanning cycle, the amplitude of the signal curve 11 is analysed to detect whether it exceeds or falls short of one of the tolerance limits 12, 17, 19 or 13, 18, 20. If the value of the signal 11 always remains either outside the tolerance limit 12 or tolerance limit 13 for more than a certain number of scanning cycles, then this is no longer a defect of short length expansion but a defect of average length expansion. The limit between longitudinal zone 27 and 28 can be considered as a limit between yarn errors of short and average length expansion. As soon as the signal curve is located within the longitudinal zone 28 and at the same time still outside either the upper tolerance limit 12 or the lower tolerance limit 13, then according to the invention, a rougher analysis criterion can be used in that for example only respectively each second or third scanning value or an average of these is studied for exceeding one of the tolerance limits 12, 17, 19 or 13, 18, 20, resulting in a reduced signal processing requirement in the sense of a reduced complexity. Correspondingly, longitudinal zone 29 for example corresponds to yarn defects of greater length expansion with a correspondingly reduced signal processing requirement again in respect of longitudinal zone 28. With the invention, a rougher analysis criterion can again be expanded in that, for example, only respectively each fourth, fifth or more remote scanning cycle or an average of these is studied for exceeding one of the tolerance limits 12, 17, 19 or 13, 18, 20, whereby it again corresponds to a reduced signal processing requirement, for yarn defects of greater longitudinal expansion, in the sense of a complexity decrease.

Figure 4:
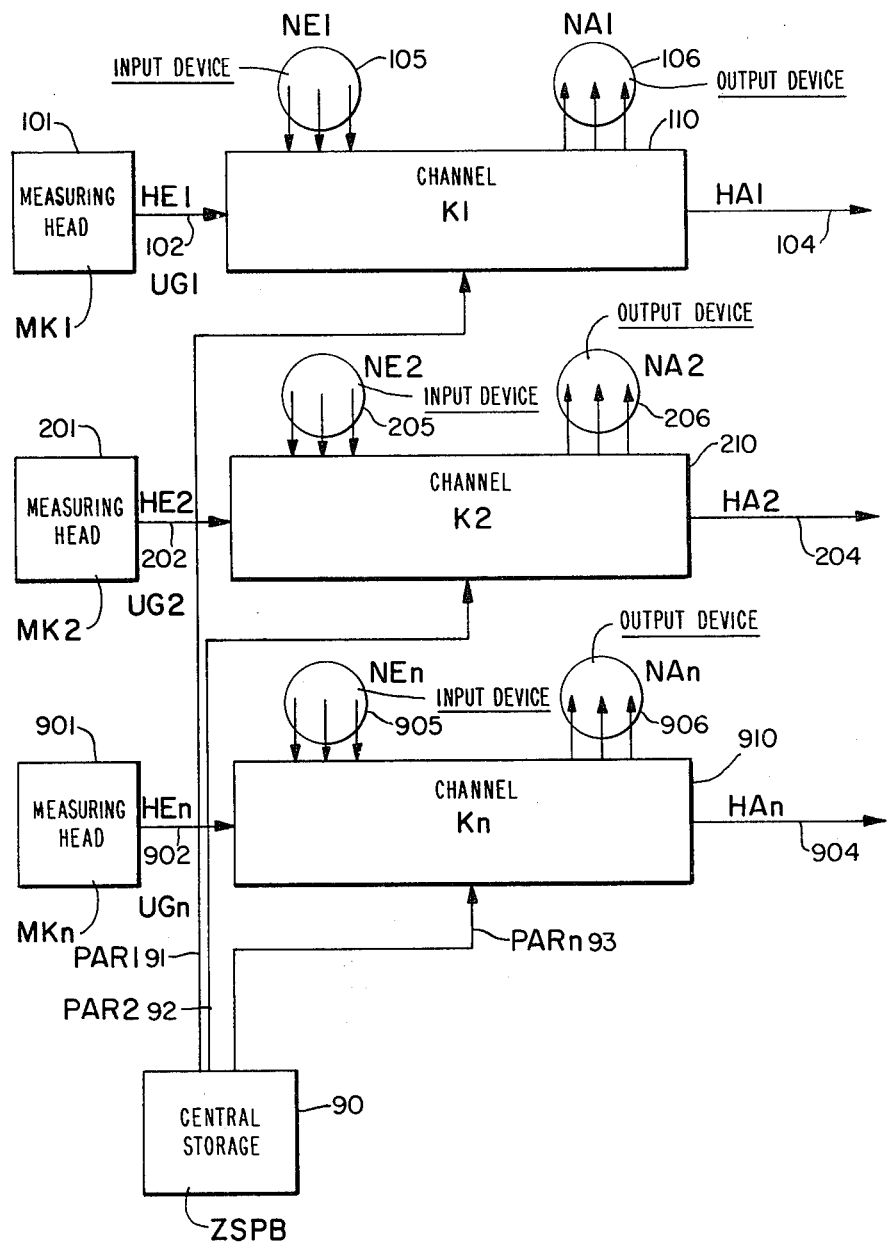
FIG. 4 is a diagram which illustrates the principle of the process processing and data storage for the evaluation.

FIG. 4 illustrates a possible use of the method according to the invention in the principal scheme of an apparatus for cleaning yarns electronically and classifying yarn defects.

The apparatus as shown in FIG. 4 comprises n channels K1 110, K2 210, Kn 910, each of which is connected to a section comprising n winding points of a winding machine. Each of these channels is fed at its main input HE1 102, HE2 202, HEn 902, by a measuring head MK1 101, MK2 201, MKn 901, by using a yarn sensor, which produces a tension UG1, UG2, UGn, the value of which is at anytime a measurement for the cross section (or diameter) of the continuously scanned yarn. Each of these channels also comprises a main output HA1 104, HA2 204, HAn 904, where a signal appears which can be used for controlling a yarn dividing apparatus according to the known technology. Each channel also comprises auxiliary inputs NE1 105, NE2 205, NEn 905 (for external severing orders, run/-stop signal etc.) as well as a number of auxiliary outputs NA1 106, NA2 206, NAn 906 for statistical data about the production of the corresponding winding points (yarn severing statistics, yarn defect statistics, halting times of the winding point) or control or warning functions derived therefrom. All the channels also have access to a central storage area ZSPB 90, where the diverse parameters PAR1 91, PAR2 92, PARn 93 which are necessary for signal analysis or resolving control and warning functions, are stored (tolerance limits for transverse and longitudinal dimension, defect assessment criteria, control and warning criteria, possibly logarithm table, yarn number, material characteristics etc.).

Figure 5:
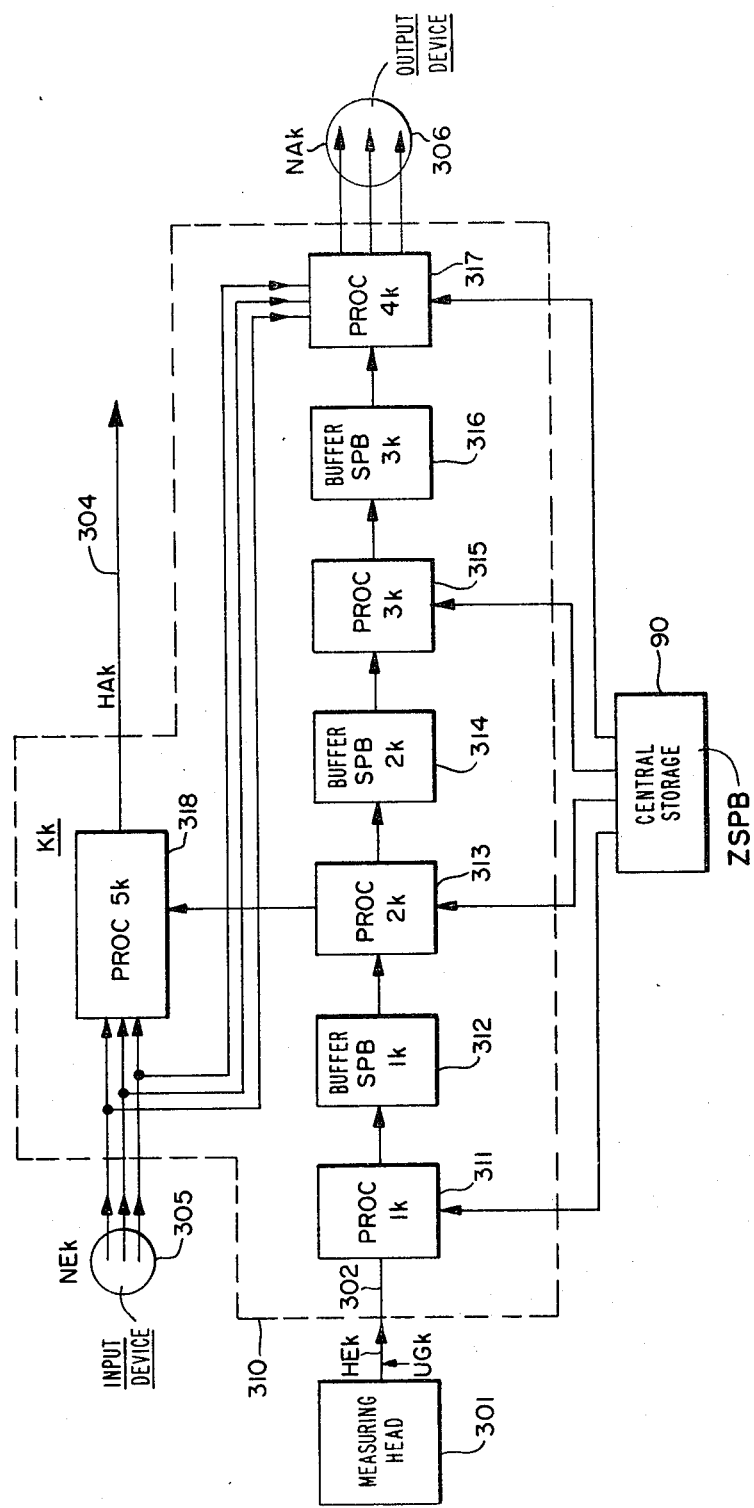
FIG. 5 is a diagram illustrating a transmission channel.

FIG. 5 illustrates one of these channels by itself. A kth measuring head MKk 301 ("k" being any one of an indefinite number of channels) is connected to a primary processor PROC1K 311 which is connected in turn to a primary storage area SPB1k 312. This is in turn connected to a second processor PROC2k 313, which is connected with a second storage area SPB2k 314. This is connected in turn with a third processor PROC3k 315, which is connected in turn to a third storage area SPB3k 316, and this is finally connected to a fourth processor PROC4k 317. Auxiliary outputs NAk 306 are connected to this fourth processor PROC4k 317. There is also a direct connection from the second processor PROC2k 313 to a severing resolution processor PROC5k 318. The output of the severing trigger processor PROC5k 318 is the main output HAk 304, i.e. the severing trigger signal. The side inputs NEk 305 also lead to the severing trigger processor PROC5k 318 in addition to the fourth processor PROC4k 317. All the processors also have access to the central storage area ZSPB 90. The auxiliary inlets NEk 305 run parallel to the severing trigger processor PROC5k 318 and to the fourth processor PROC4k 317, the auxiliary outputs NAk 306 exit from the fourth processor PROC4k 317.

The function of the apparatus shown in FIG. 4 will now be explained with the kth channel (FIG. 5).

The measuring head MKk 301 releases a temporally variable direct current UGk, which is proportional to the respective cross section (diameter) of the yarn passing through the measuring head MKk 301. This direct current is sampled in the first processor PROC1k 311, during discrete time intervals and is digitalised in 16 bit words. Also, the digitalised yarn signal is converted in the first processor PROC1k 311 from the linear scale into the logarithmic scale by means of a logarithm table (table-look-up method) stored in the central storage area ZSPB 90 and reduces the word length simultaneously from 16 bits to 8 bits. The temporal dependence of the digitalised yarn signal is also eliminated in the first processor PROC1k 311 in that the clock frequency of the analog/digital conversion is made proportional to the speed of the yarn moving through the measuring head. This is effected according to FIG. 5 by using the predetermined value stored in the central storage area ZSPB 90 of the winding velocity used for the relevant winding point or alternatively in a known manner by a direct synchronisation (not shown in FIG. 5) e.g. with the rotating velocity of the grooved cylinder positioned at the winding point. Furthermore, in the first processor PROC1k 311, the yarn signal is normalised to a constant nominal cross section (diameter) and constant (dielectric) yarn characteristics. The corresponding values (yarn number, material figure) are delivered by the central storage area ZSPB 90. Since these values act by multiplication on the signal proportional to the yarn cross section (diameter), its consideration results in the yarn signal which is represented in the logarithmic measure, in simple addition or subtraction, which in addition to the reduced word length indicates a considerable simplification by the representation according to the invention of the yarn signal on the logarithmic scale. After all these conversions, a sequence of normalised values from the first processor PROC1k 311 is entered in the first storage area SPB1k 312, whereby the scanned yarn has advanced at a constant speed from one value to the next independent of the winding velocity. The values entered in the first storage area SPB1k 312 are therefore normalised to a cross section (diameter) "one" and are now exclusively dependent on the relative diameter of the yarn and on the wound length.

The storage areas SPB1k 312, SPB2k 314, SPB3k 316 are all according to FIG. 5 implemented in terms of hardware so-called FIFO memories (first-in, first out). Other software-oriented storage methods can also be considered within the scope of the method according to the invention whereby the memory position administration would be effected by a memory position administration process not shown in FIGS. 4 and 5.

In a second processor PROC2k 313, continuous values are removed from the first storage area SPB1k 312 and are subjected to a signal analysis process. This signal analysis process consists in that each individual one of the normalised cross section values is studied to ascertain whether it has exceeded or fallen short of one of the defect tolerance limits which are stored in the central storage area ZSPB 90, or whether it is in the same tolerance zone as its predecessor. The relative yarn deviation will lie most frequently within the lowest defect tolerance limit so that it is no longer necessary to study this value further. A more detailed analysis is only justified when one of the mentioned tolerance limits is exceeded. According to how long the signal remains in one defect zone and in which defect zone the signal value is located at the time, a yarn defect which is to be potentially cleaned is present. If this is the case, the second processor PROC2k 313 informs the severing trigger processor PROC5k 318. This processor, independent of the second processor PROC2k 313 then investigates whether a yarn cut is justified or not as a result of the signals present at the auxiliary inputs NEk 305. In a relevant case, a severing order is emitted from the severing trigger processor PROC5k 318 to the main output HAk304.

For the purpose of yarn defect classification (severed and unsevered yarn defects) the yarn signal has to be analysed according to finer criteria than is necessary for yarn defect cleaning. However it is sufficient, as hereinbefore mentioned, if it is established that the yarn deviation has entered into a new tolerance zone or has left a tolerance zone. This entry/exit into a new tolerance zone is also controlled by the second processor PROC2k 313. Each time a relatively rare event of this type takes place, it is represented in the second storage area SPB2k 314 in a suitably coded form by stating what has happened and at which yarn length this has taken place. The second storage area SPB2k 314 is therefore constantly fed with one or more data words which contain such changes of condition as well as the position on the winding machine where they appeared.

In a third processor PROC3k, a yarn defect classification is effected, for example, according to a table scheme ("Uster Classimat" (Registered Trade Mark) principle) from these values in a known manner. The parameters necessary for this classification are removed from the central storage area ZSPB 90 if they have not already been used in the second processor PROC2k 313. The completely classified yarn defects are coded in a suitable form by the processor PROC3k 315 by stating the position where they appeared on the yarn and are stored in a third storage area SPB3k 316.

In a fourth processor PROC4k 317, these classified yarn defects set down in the third storage SPB3k 316 are then combined in a known manner into messages together with the condition details introduced via the auxiliary inputs NEk 305 concerning the behavior of the winding point and the cleaner and are processed further.

In conclusion it can be established that in an apparatus according to FIGS. 4 and 5, for each channel 5 asynchronous processes take place which are decoupled from each other by storage areas functioning as buffers, which are particularly convenient in that they can be produced with a minimum technical complexity conditioned by the subjective perception.

As a result of the method of the invention, a skilled man will let certain processes take place in practice, according to use and relations, on one or more common processors. Assuming an apparatus constructed from n channels according to FIGS. 4 and 5, it will be advantageous in certain cases to implement for example the similar processes PROC11, PROC1k to PROC1n on a processor specifically intended for this purpose, and also the similar processes PROC21, PROC2k to PROC2n on another dedicated processor intended specifically for this purpose and the remaining similar processes PROC31, PROC3k. . . , and PROC3n and PROC41, PROV4k . . . , PROC4n, and PROC51, PROC5k . . . , PROC5n respectively of another common dedicated processor. It could be advantageous for the first two groups to construct specific processors with components of the so-called bit-slice-technology and to use a universal micro processor or micro computer for the processes of the last group.

Within the scope of the invention it may also be advantageous to implement all the processes of at least one channel on a common processor or to carry out certain parts in the traditional digital constructional method. It is also self evident that the various storage areas represented as FIFO buffer stores in terms of hardware can also be installed on one or more addressable memories, whereby—as already pointed out above—a specific (common) process which is not shown in FIGS. 4 and 5 is to be provided for the storage position administration.

I claim:

1. A method of assessing yarn defects using digital technology comprising the steps of generating analog yarn signals proportional to the running yarn cross section or diameter by means of one or more sensors; converting said yarn signals to digital signals on a logarithmic scale representing periodic samples of said yarn cross section or diameter; analyzing said digital signals with respect to the relative deviations thereof from set values and from the digital signal representing the previous sample to detect those digital signals which fall outside a given lowest tolerance range and determine the extent to which those digital signals lie outside said lowest tolerance range or deviate from the previous sample in terms of successive tolerance zones; and controlling the cleaning of the yarns on the basis of the results of analyzing said digital signals.

2. A method according to claim 1, wherein said step of analyzing said digital signals includes comparing only said digital signals which fall outside said given lowest tolerance range to a plurality of selected defect tolerance limits which define said successive tolerance zones to determine the extent of the relative deviation thereof.

3. A method according to claim 2, wherein said step of analyzing said digital signals includes comparing only said digital signals which fall outside said given lowest tolerance range to the digital signal representing the previous sample to detect changes in tolerance range.

4. A method according to claim 2, wherein said step of analyzing said digital signals includes comparing said digital signals to said plurality of selected defect tolerance limits and to the digital signal representing the previous sample to detect whether the relative deviation has entered or left a particular deviation zone or was already present in that deviation zone on the basis of the previous sample.

5. A method according to claim 2, wherein said step of analyzing said digital signals includes comparing only said digital signals relating to each Mth sample (where M is an integer greater than one) with said tolerance limits.

6. A method according to claim 2, wherein said step of analyzing said digital signals includes comparing only an average of each M samples (where M is an integer greater than one) with said tolerance limits.

7. A method according to claim 7, wherein the analysis of the statistical deviations established by at least one sensor is arranged into at least two successively-performed processes such that data from the previously-performed process is written in a memory and is then read back when this data is required for further processing in the subsequently-performed process.

8. A method according to claim 1, further including the step of normalizing said digital signals prior to said analyzing.

9. A method of assessing yarn defects using digital technology comprising the steps of generating analog signals proportional to the running yarn cross section or diameter by means of one or more sensors; converting said analog signals to digital signals representing periodic samples of said yarn cross section or diameter on a linear scale; converting said digital signals from a linear scale to a logarithmic scale; storing the converted logarithmic digital signals; comparing said stored converted logarithmic digital signals to a plurality of selected defect tolerance limits which form successive tolerance zones outside of a given minimum tolerance zone and to the digital signal representing the previous stored sample; storing only those digital signals which fall outside said given minimum tolerance zone and represent an entry into or an exit from a given tolerance zone on the basis of the previous sample; and generating a trigger command for yarn cleaning in response to selected digital signals which are identified in said comparing step as relating to yarn defects.

10. A method of assessing yarn defects according to claim 9, further comprising classifying said yarn defects on the basis of the digital signals stored in said second storing step.

11. A method of assessing yarn defects according to claim 10, further comprising coding and storing said classified yarn defects.

12. A method of assessing yarn defects according to claim 9, further including normalizing said converted digital signals.

* * * * *